(12) United States Patent
Hommann

(10) Patent No.: US 8,591,465 B2
(45) Date of Patent: Nov. 26, 2013

(54) DEVICE FOR ADMINISTERING AN INJECTABLE PRODUCT

(75) Inventor: Edgar Hommann, Grossaffoltern (CH)

(73) Assignee: TecPharma Licensing AG, Burgdorf (CH)

( * ) Notice: Subject to any disclaimer, the term of this patent is extended or adjusted under 35 U.S.C. 154(b) by 1137 days.

(21) Appl. No.: 11/417,518

(22) Filed: May 4, 2006

(65) Prior Publication Data

US 2006/0264830 A1 Nov. 23, 2006

Related U.S. Application Data

(63) Continuation of application No. PCT/CH2004/000645, filed on Oct. 28, 2004.

(30) Foreign Application Priority Data

Nov. 5, 2003 (DE) .................................. 103 51 594

(51) Int. Cl.
*A61M 37/00* (2006.01)

(52) U.S. Cl.
USPC .............................. 604/131; 604/134; 604/194

(58) Field of Classification Search
USPC .................................. 604/110, 131, 134, 194
See application file for complete search history.

(56) References Cited

U.S. PATENT DOCUMENTS

| | | | |
|---|---|---|---|
| 4,316,463 A * | 2/1982 | Schmitz et al. | 604/135 |
| 5,695,472 A * | 12/1997 | Wyrick | 604/136 |
| 6,805,686 B1 * | 10/2004 | Fathallah et al. | 604/135 |
| 2003/0171717 A1 | 9/2003 | Farrugia et al. | |
| 2004/0039336 A1 * | 2/2004 | Amark et al. | 604/136 |

FOREIGN PATENT DOCUMENTS

| | | | |
|---|---|---|---|
| WO | WO 02/47746 A1 * | 6/2002 | |
| WO | WO200247746 | * | 6/2002 |
| WO | WO 03/070296 A2 | 8/2003 | |

* cited by examiner

*Primary Examiner* — Kevin C Sirmons
*Assistant Examiner* — Deanna K Hall
(74) *Attorney, Agent, or Firm* — Dorsey & Whitney LLP; David E. Bruhn, Esq.

(57) ABSTRACT

A device for administering an injectable product, including a housing, a displaceably mounted product container accommodated by the housing, a plunger in the container so that it can be displaced in a forward-drive direction in order to dispense the product, a plunger rod acting on the plunger in the forward-drive direction and having a releasable retained position, and a spring acting on the plunger rod in the forward-drive direction, the plunger rod releasably held in the retained position in a retaining engagement against the force of the spring, wherein the spring projects into the container in the retained position.

23 Claims, 3 Drawing Sheets

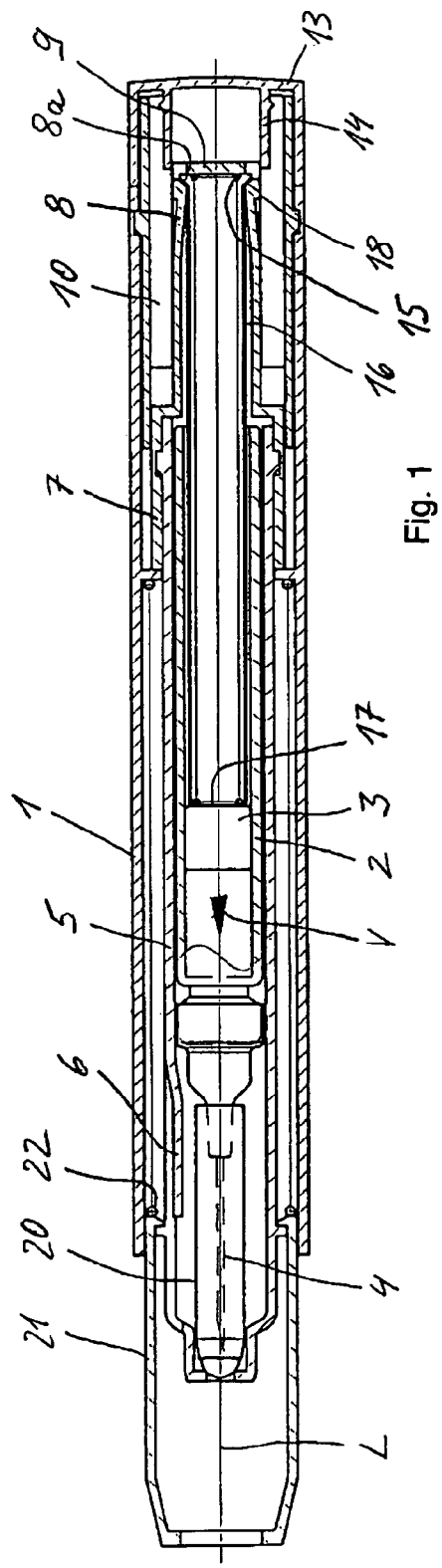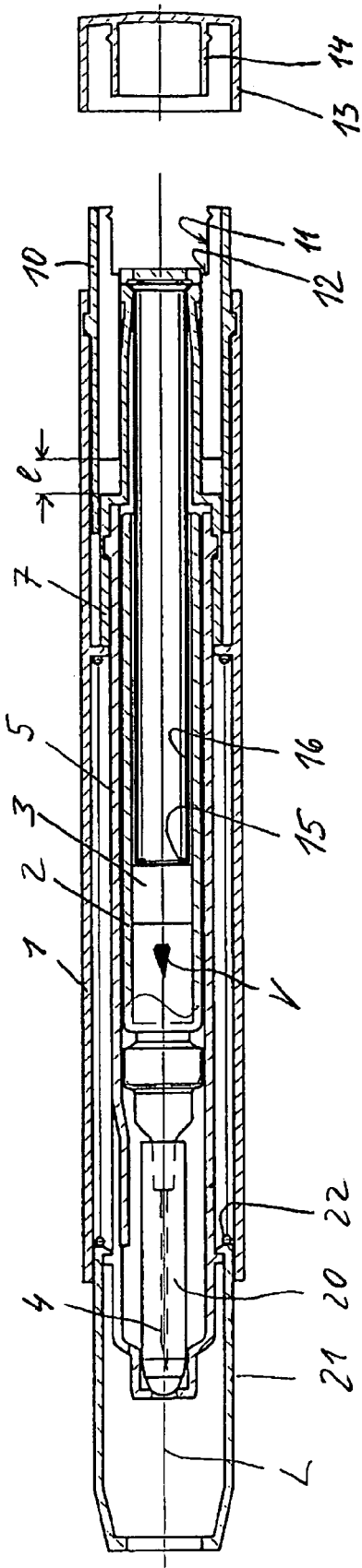

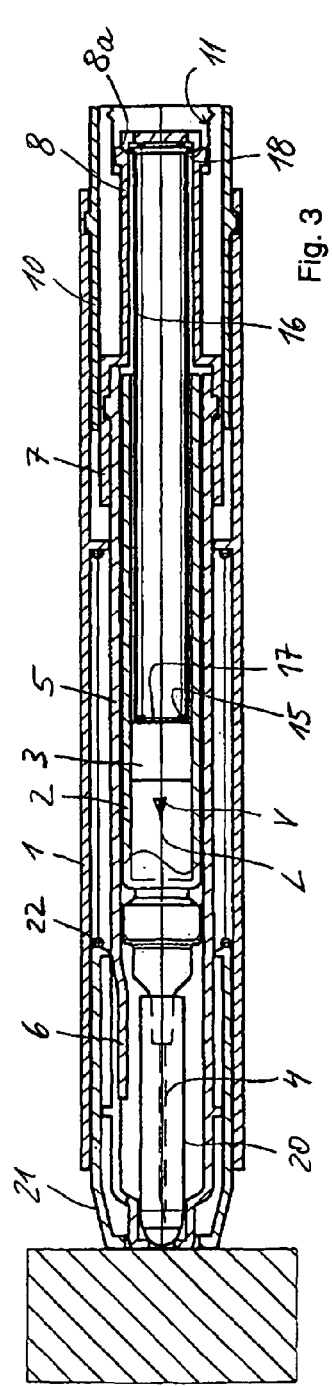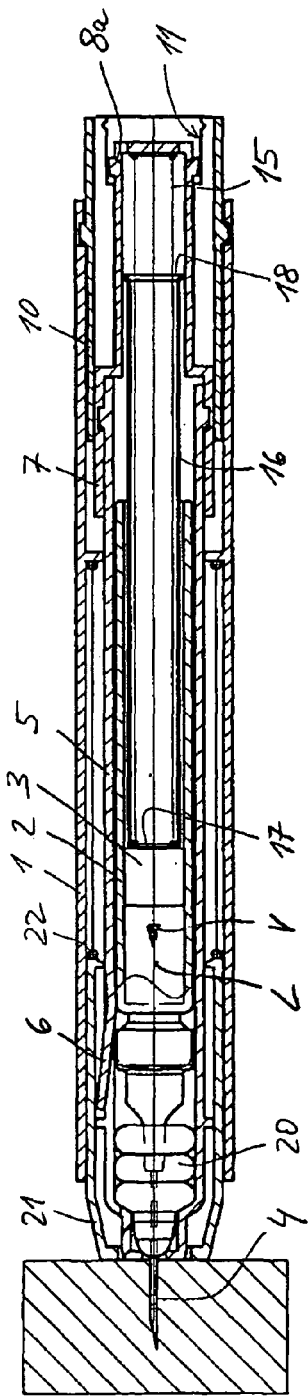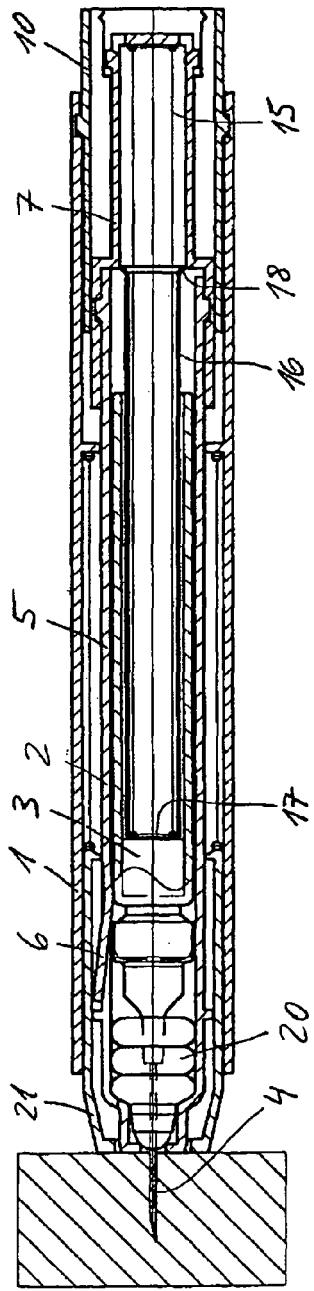

DEVICE FOR ADMINISTERING AN INJECTABLE PRODUCT

CROSS-REFERENCE TO RELATED APPLICATION(S)

This application is a continuation of International Application No. PCT/CH2004/000645, filed on Oct. 28, 2004, which claims priority to German Application No. 103 51 594.1, filed on Nov. 5, 2003, the entire contents of both of which are incorporated herein by reference.

BACKGROUND

The invention relates to devices for administering, injecting, delivering or dispensing substances, and to methods of making and using such devices. More particularly, it relates to a device for administering an injectable product wherein the device may be an automatic injector.

Injection devices of the type to which the invention relates are known from DE 198 22 031 B and U.S. Pat. No. 4,031,893. Both documents describe automatic injectors. In the case of the automatic injector disclosed in DE 198 22 031 A1, a mechanical sequence controller ensures that once the device has been triggered, the injection cannula is inserted through the skin to the desired depth in a first phase and the product to be injected is not dispensed and administered until a subsequent second phase. The injection device disclosed in U.S. Pat. No. 4,031,893 does not have such a sequence controller. Instead, a drive mechanism applies pressure to push a plunger disposed in a container filled with the product, and both the container and hence also the injection cannula and the plunger in the container are pushed in a forward direction due to static friction. The insertion and dispensing procedures do not, therefore, take place exactly sequentially and instead also take place simultaneously to a certain extent.

The plunger of the respective devices is driven forwards by means of a plunger rod and a spring acting on the plunger rod in the forward-drive (or injection or delivery) direction of the plunger. In the case of the devices disclosed in DE 198 22 031 A1, the spring is accommodated in a drive cup and pushes the cup against a proximal end of the plunger rod. In the simplified design disclosed in U.S. Pat. No. 4,031,893, the spring directly surrounds the plunger rod and pushes in the forward direction against a shoulder of the plunger rod which projects radially outwards. The plunger rod is either fixedly connected to the plunger directly or is connected to an intermediate piece fixedly connected to the plunger, which serves as an adapter for adapting to different filling levels of the container.

In order to improve handling, it is desirable to make devices for administering injectable products as compact as possible, and, in particular, with as short as possible a length as measured in the forward-drive direction of the plunger. This is particularly desirable in the case of automatic injectors because automatic injectors are generally longer than conventional injection devices, including simple syringes, simply because the injection cannula has to be moved an extra distance in the forward-drive direction relative to a housing to account for the insertion depth desired for the injection.

SUMMARY

In one embodiment, the present invention provides a way of shortening devices for administering an injectable product.

In one embodiment, the present invention comprises a device for administering an injectable product comprising a housing, a displaceable product container accommodated by the housing, a plunger in the container so that the plunger can be displaced in a forward-drive direction to administer the product, a plunger rod acting on the plunger in the forward-drive direction and having a releasable retained position, and a spring acting on the plunger rod in the forward-drive direction, the plunger rod releaseably held in the retained position in a retaining engagement against the force of the spring, wherein the spring projects into the container in the retained position.

In one embodiment, the present invention comprises a device for administering an injectable product comprising a housing, a container for the product mounted or carried by the housing and incorporating a plunger, a plunger rod and a spring acting on the plunger rod. When the plunger is moved in a forward-drive direction (which also might be thought of as the injection or delivery direction), the product is dispensed from the container. Accordingly, the spring acts on the plunger rod in the forward-drive direction. The plunger rod and the spring are constituent components of a drive unit for the plunger or constitute such a drive unit on their own. The device may also have an injection cannula, which points in the forward-drive direction.

When the device is in an initial state, for example immediately before administering a product, the device is "armed", i.e. the spring is tensed, and the plunger rod is held in a retained position in a retaining engagement against the force of the tensed spring. The retaining engagement may be effected directly between the housing and the plunger rod or, in some preferred embodiments, between these two components but initially via one or more transmitting elements. The retaining engagement is releasable.

In some embodiments, the spring extends into the container and does so not just during the dispensing movement but already when the device is in an initial state prior to triggering the drive unit. The plunger does not usually terminate in a flat arrangement with what is the rear edge of the container by reference to the forward-drive direction, which means that a space is left free between the plunger rear face and the rear edge of the container. The present invention makes use of this space as a means of accommodating at least a part of the axial length of the spring extending in the forward-drive direction. Compared with the known devices, therefore, the overall axial length of the device can be made shorter by the length by which the spring projects beyond the rear edge of the container in the forward-drive direction when the plunger rod is already in the retained position. If the plunger terminates in a flat arrangement with the rear container edge, it follows that the plunger will form a cavity into which the spring and accordingly also the plunger rod project.

The device of the present invention may be any injection device, including, for example, in some preferred embodiments, an injection pen. Since the spring acts on the plunger rod in the forward-drive direction, a user of the device does not have to effect the dispensing movement, i.e., the forward-drive movement of the plunger rod and the plunger. The user merely has to trigger the drive unit, which then automatically drives the plunger in the forward-drive direction.

In some preferred embodiments, the device is an automatic injector, which, when triggered, not only automatically effects the dispensing movement but also an insertion movement in the forward-drive direction for an injection cannula connected to the product container. However, the injector need not necessarily have an injection cannula. It would also be conceivable to administer the product by way of a so-called pressure injection. If the automatic injector has an injection cannula, e.g., for a subcutaneous injection, the drive unit may incorporate an additional spring, which acts as an injection spring and causes the piercing movement of the injection cannula, whereas the other spring fulfils the function of a dispensing spring which causes the dispensing movement, i.e., the forward drive of the plunger in the container. In some preferred embodiments, said spring is an injection and dispensing spring in one.

In some preferred embodiments, the device in accordance with the present invention is used for self-administering products. Applications or uses include, for example, diabetes treatment, osteoporosis therapy and treatment with growth hormones. Accordingly, the injectable product is insulin, an osteoporosis preparation or a growth hormone, for example.

In some preferred embodiments, the plunger rod may be fixedly connected to the plunger and, in others, it pushes loosely against the plunger rear face. In one preferred embodiment, it has a ram, by means of which it pushes against the plunger rear face when effecting the dispensing movement, thereby moving the plunger in the forward-drive direction. The spring may be supported against the rear face of the ram. To save axial length, the ram should form the front end of the plunger rod and is slim, in some embodiments having a thickness of less than 2 mm. The spring is supported directly on the rear face of the ram, so that its front end is spaced back from the plunger rear face by only the thickness of the ram when the ram is pushing against the plunger rear face. The ram is already in contact with the plunger rear face when the plunger is in the retained position.

In some preferred embodiments, the plunger rod guides the spring axially. This being the case, the spring may surround the plunger rod. In some preferred embodiments, however, the plunger rod surrounds the spring. In these embodiments, the plunger rod is a sleeve, which may be circular cylindrical, with a sleeve exterior which may be discontinuous but continuously smooth. A shoulder is provided on a front end of the sleeve, projecting radially inwardly from the sleeve exterior, against which the spring is supported in the forward-drive direction, and which also forms said ram. Accordingly, the shoulder should form the front end of the sleeve exterior. The shoulder may form a base of the sleeve, which in this instance is cup-shaped. Instead, however, it may also be provided in the form of a circumferentially extending annular shoulder. It may take the form of a web projecting radially inwards and, in such an embodiment, several of the shoulders project radially inwardly from the sleeve exterior in order to support the spring as uniformly as possible around the sleeve periphery.

For the purposes of the retaining engagement, in some preferred embodiments, the plunder rod has a retaining shoulder, which is in a retaining engagement with a complementary shoulder of the housing or a support structure disposed between the housing and the plunger rod. The retaining shoulder may be in abutting contact with the complementary shoulder in the forward-drive direction directly or indirectly via a transmitting mechanism, such as a ball bearing or a cylindrical pin or several such bodies, for example. When the device is triggered, the block on the plunger rod caused by the abutting contact is released so that the plunger rod is driven in the forward-drive direction by the force of the spring.

In some preferred embodiments, the retaining shoulder is provided in the form of a conically shaped widening of the plunger rod. The plunger rod merges with the widening at its rear end. If the plunger rod is a sleeve, as in some preferred embodiments, it advantageously extends in a funnel-shaped arrangement forming the widening, i.e., it forms an axial, short open funnel at its rear edge.

In one preferred embodiment, the plunger rod is therefore a sleeve, the front end of which forms an inwardly protruding shoulder in the form of a closed base or an annular shoulder.

In order to be able to hold the plunger rod in a retained position against the force of the spring, the plunger rod is also provided with at least one generally circumferentially extending, retaining shoulder, as mentioned above, in other preferred embodiments. Optionally, however, several individual retaining shoulders may be distributed around the periphery of the sleeve. This design of the plunger rod is already advantageous, even without other features of the present invention, according to which the spring already extends into the container when the plunger rod is in the retained position.

In an alternative embodiment, in which the plunger rod likewise forms a sleeve, the shoulder serving as a support for the spring and also the ram project outwards from the shaft portion of the sleeve. In this embodiment, the spring surrounds the sleeve. In an embodiment where one is provided, the retaining shoulder may project radially inwardly beyond the sleeve shaft at the oppositely lying end of the sleeve, in order to establish a retaining engagement with a complementary shoulder projecting into the sleeve, in which case the retaining engagement between the shoulders is that where the sleeve surrounds the spring.

In one embodiment, the present invention comprises an administering device incorporating a plunger rod in the form of a sleeve, wherein the spring does not necessarily project into the product container.

The plunger rod provided in the form of a sleeve may be made in a single piece from a metallic or other suitable material. in some preferred embodiments, it is made from a semi-finished product by re-shaping. A suitable semi-finished product would be tubes, for example, which can be cut to the appropriate length for the plunger rod by means of a cutting process to form tube pieces. The shoulder on which the spring is supported and, if provided, also the retaining shoulder, is or are formed by re-shaping a tube piece end or both tube piece ends. A shoulder projecting radially outwards and also a shoulder projecting radially inwards from the sleeve shaft can be obtained by a bending process using a die. Another suitable forming process would be deep-drawing, in which case the semi-finished product would be a plate-type semi-finished product. By deep-drawing, a cup-shaped plunger rod with a shoulder extending round the open end of the cup can be produced by deep-drawing in particular.

It should be appreciated that any of the embodiments, features, functions and/or structures described herein may be used cooperatively and/or to complement each other.

BRIEF DESCRIPTION OF THE DRAWINGS

FIG. 1 depicts one embodiment of an injection device in accordance with the present invention, an automatic injector in an initial state, in which a drive unit of the injector is tensed and secured, FIG. 2 shows injection device of FIG. 1 with the drive unit tensed but unlocked, FIG. 3 shows the injection device of FIG. 1 positioned on an injection site directly before piercing by an injection cannula, FIG. 4 illustrates injection device of FIG. 1 immediately after piercing by the injection cannula and immediately before dispensing the product, FIG. 5 shows the injection device of FIG. 1 with the inserted injection cannula after dispensing the product.

DETAILED DESCRIPTION OF THE DRAWINGS

Figure 6:
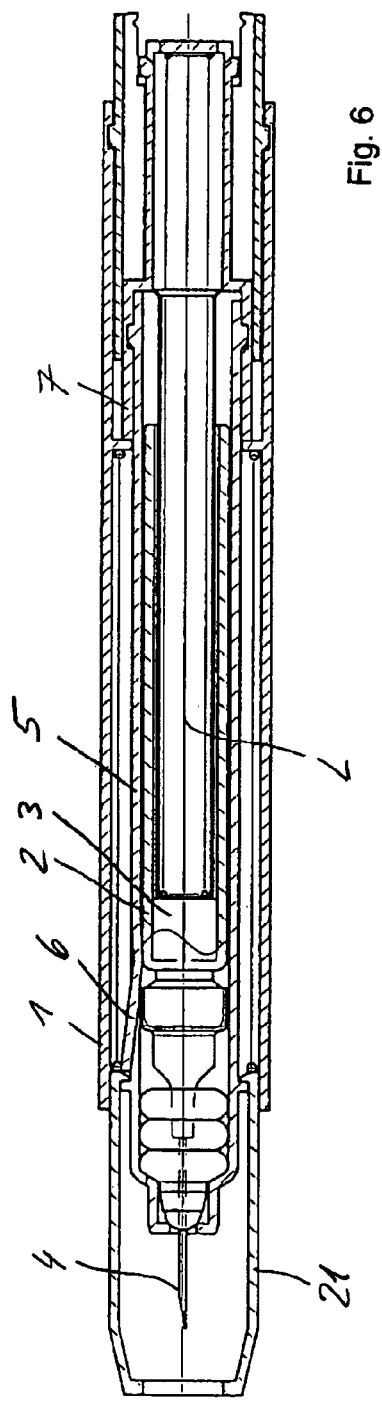
FIG. 6 shows the injection device of FIG. 1 after use.

FIG. 1 illustrates an embodiment of an injection device in accordance with the present invention, wherein the device is an automatic injector. The injector is depicted in section through a longitudinal plane, which has a central axis of symmetry L of the injector, which is referred to below as longitudinal axis L.

A casing structure 1 forms a main part of a housing of the injector. The casing structure 1 serves as a means of holding the injector and mounting its components. The casing structure 1 is a circular cylindrical sleeve with the longitudinal axis L as its axis of symmetry. A support structure is accommodated in the casing structure 1, which can be displaced relative to the casing structure 1 along the longitudinal axis L. The support structure comprises two parts and consists of a distal part 5 and a proximal part 7, which are connected to one another so that they are unable to move axially relative to one another. The support structure as a whole is a generally hollow cylinder in the embodiment illustrated, but other configuration are possible. A container 2 filled with an injectable product is accommodated in the support structure so as to be axially displaceable relative to the support structure in a forward-drive direction V. The container 2 is an ampoule. The product is in the container 2, mounted between an outlet which the container 2 has at an end disposed at the front end (which also may be thought of as the injection, delivery, distal or needle or cannula carrying end) by reference to the forward-drive direction, and a plunger 3, which is accommodated in the container 2 so that it can slide axially. Attached to the front end of the container 2 is an injection cannula 4, pointing in the forward-drive direction V. A dispensing movement of the plunger 3 in the forward-drive direction V forces the product out of the container 2 and then dispenses it through the injection cannula 4.

The dispensing movement of the plunger 3 is generated by means of a drive unit. The drive unit consists of a mechanical spring 15 and a plunger rod 16. At its front end face, the plunger rod 16 forms a ram 17, by means of which it pushes against the plunger 3 in the forward-drive direction V. There is no connection between the plunger rod 16 and the plunger 3 other than the pressing contact.

In the state illustrated in FIG. 1, the plunger rod 16 has assumed an axial retained position, in which it is retained against the force of the tensed spring 15 acting in the forward-drive direction V. To this end, the plunger rod 16 is in a retaining engagement with the support structure. The support structure is in turn prevented from moving in the forward-drive direction V relative to the casing structure 1 due to a form fit. The form fit exists between a front edge of the proximal part 7 and a shoulder projecting inwardly from a casing internal surface of the casing structure 1. A spring 22 presses the support structure into this abutting contact with the casing structure 1.

The retaining engagement of the plunger rod 16 exists directly between a retaining shoulder 18 of the plunger rod 16 and a complementary shoulder 8a of the proximal part 7 of the support structure. At its proximal (or rear) end, the plunger rod 16 mergers into a wider conical region constituting the retaining shoulder 18. The sleeve-shaped proximal part 7 is axially slotted so that tab-type retaining elements 8 are formed, each with a free proximal end. The retaining elements 8 are able to bend elastically. Each of the retaining elements 8 forms one of the complementary shoulders 8a for the retaining shoulder 18 at its free proximal end. The complementary shoulders 8a lie facing the retaining shoulder in the forward-drive direction. The retaining shoulder 18 sits in direct abutting contact with the complementary shoulders 8a.

In the retained position, the retaining elements 8 are blocked (or locked) in the retaining engagement by means of a blocking (or locking) mechanism 10. The blocking mechanism 10 is connected to the casing structure 1 so that it can not be displaced axially. In the exemplary embodiment illustrated, it is inserted in the casing structure 1 through the open proximal end of the casing structure 1 and latches with the casing structure 1. The blocking mechanism 10 is a sleeve body and surrounds the retaining elements 8 and blocks the retaining elements 8 in the retaining engagement, insofar as it prevents the retaining elements 8 from flexing radially outwards under the pressure exerted by the spring 15 via the retaining shoulder 18. The retaining elements 8 are thicker radially towards the exterior at their free proximal ends, so that they are bent against a radially facing, oppositely lying blocking surface of the blocking mechanism 10 radially inwards into the retaining engagement. The blocking surface is a casing internal face of the blocking mechanism 10.

In the retained position, the spring 15, a compression spring in the illustrated embodiment, is placed under pressure between a proximal spring support 9 and the ram 17, which therefore forms a distal spring support.

In the retained position, the spring 15 extends from the proximal spring support 9 into the proximally open container 2 and projects virtually as far as the plunger 3. Its distal end is spaced axially apart from the rear face of the plunger 3 by only the thickness of the ram 17. The ram 17 in turn forms a thin, flat base of the plunger rod 16 pointing radially towards the longitudinal axis L. The spring 15 is therefore applied as closely as possible against the plunger in order to obtain a drive unit and ultimately an injector with as short as possible an axial length. In some embodiments, the ram 17 ideally has a thickness which is precisely that needed to support the tensed spring 15. The lower limit for the thickness of the spring support formed by the ram 17 may, therefore, be predefined solely by the actual strength needed and a bit extra needed for safety reasons.

In embodiments of the present invention comprising slim containers 2 with a correspondingly small cross-section, it is advantageous if the plunger rod 16 is a metal sleeve. With a slimmer wall thickness, metal sleeves are stronger than plastic parts. The spring 15 lying against the sleeve shaft of the plunger rod 16 and guided by the sleeve shaft may be of a correspondingly thicker design. The spring stiffness and hence the spring force exerted during the forward-driving action may advantageously be higher than is the case with thick-walled sleeves. For a pre-defined hollow cross-section of the container 2, therefore, sleeves with a slimmer wall thickness may be preferred for the plunger rod 16. The bigger the cross-section of the container 2 is, the plunger rod 16 may be designed with a correspondingly larger external circumference. If the hollow cross-section of the container 2 exceeds a specific size, the plunger rod may 16 may also be a plastic sleeve in the embodiment where a sleeve is used.

In some embodiments, the plunger rod 16 is a metal sleeve deep-drawn from a plate-type semi-finished product. It extends axially from the plunger 3 almost as far as the spring support 9, and is spaced apart from the spring support 9 by only the axial distance needed for the engagement of the complementary shoulders 8a. When the spring 15 is in the tensed state, the spring 15 and the plunger rod 16 are therefore essentially of the same axial length. The spring support 9 in the form of the sleeve base constitutes the end of the support structure.

The housing of the injector formed by the casing structure 1 and the blocking mechanism 10 are terminated by a locking element 13, which, in the embodiment illustrated as an example, is a locking cap. The locking element 13 is detachably secured to the blocking mechanism 10 by means of a catch system. It can be removed by the user by hand in order to unlock the injector and thus "arm it" in readiness for administering the product. In the initial state illustrated in FIG. 1, an axially projecting web 14 of the locking element 13 prolongs the blocking surface of the blocking mechanism 10 in the proximal direction.

FIG. 2 illustrates the automatic injector in the unlocked and hence "armed" state after the locking element 13 has been removed. Removing the locking element 13 exposes a recess 11 of the blocking mechanism 10. The recess 11 is formed proximally in an axial extension of the blocking surface of the blocking mechanism 10. The blocking mechanism 10 becomes wider in the forward-drive direction V from its blocking surface via a shoulder 12 into the recess 11. The shoulder 12 forms an abrupt transition from a distal portion forming the blocking surface to a proximal portion of the blocking mechanism 10 forming the recess 11. Accordingly, the web 14 of the locking element 13 is an annular web, which fills the portion of the blocking mechanism 10 forming the recess 11 up to the radial height of the blocking surface in the fitted state.

In the unlocked state, the support structure as a whole can be displaced relative to the casing structure 1 and the blocking mechanism 10 can be moved in the direction opposite the forward-drive direction V so that the retaining elements 8 move with their free proximal ends behind the shoulder 12 into the recess 11, where they can be moved radially outwards out of the retaining engagement. The travel length 1 of the backwards movement needed to achieve this is pre-defined by an abutment surface of the blocking mechanism 10 pointing in the forward-drive direction V and an axially facing complementary abutment surface of the proximal part 7 pointing in the direction opposite the forward-drive direction V.

At the distal end of the casing structure 1, a needle guard 21 projects into the casing structure 1, which is likewise open. The casing structure 1 provides a mount for or carries the needle guard 21 so that it can be axially displaced. The spring 22, which is supported on the casing structure 1 on the one hand and on the needle guard 21 on the other, biases the needle guard into a distal position relative to the casing structure 1. The spring 22 therefore pushes the needle guard 21 against a stop formed by the support structure. In its distal region, the support structure has an outwardly bendable blocking element 6, integrally formed from the distal part 5 in the form of a sort of tongue projecting in the forward-drive direction V. The purpose of the blocking element 6, after administering the product, is to block the needle guard 21 in its protective position, i.e., in its distal or forward position relative to the casing structure 1, and thus protect the user from the injection cannula 4.

A cannula cover 20 is placed on the distal end of the container 2 and over the injection cannula 4. One the one hand, the cannula cover 20 positions the container 2 in the support structure and has the requisite stiffness for this purpose. Furthermore, it helps keeps the injection cannula sterile. On the other hand, however, its axial stiffness is not so great that it could hamper or even prevent the forward driving action of the container 2 in the support structure once the injector has been triggered. The needle cover 20 may be an axially flexible rubber sleeve or a bellows, for example.

An embodiment of the operation or method of use of the automatic injector embodiment of the present invention follows.

The injector may be issued to the user in the initial state, the state as sold, illustrated in FIG. 1. The container 2 is filled with exactly the quantity of product required for one injection beforehand. The drive unit is loaded, i.e., the plunger rod 16 is disposed in the retaining engagement and the spring 15 is tensed.

By removing the locking element 13 from the blocking mechanism 10, the user unlocks the injector, which is then in the unlocked state illustrated in FIG. 2.

In the unlocked state, the injector together with the needle guard 20 is placed vertically on the skin at the desired injection site and pressed against the skin. The casing structure 1 serves as a manual grip for this purpose. As the contact pressure increases, the needle guard 21 is moved against the force of the spring 22 deeper into the casing structure 1 in a first phase of the contact pressure. As soon as the support structure has been pressed enough so that its proximal end is in contact with the skin, in a subsequent, second phase due to additional contact pressure, the needle guard 21 and the support structure are jointly moved opposite the forward-drive direction V relative to the casing structure 1. During the course of this relative movement, the retaining elements 8 slide on the blocking surface of the blocking mechanism 10 in the proximal direction, finally reaching the region of the recess 11. The relative movement is restricted by the support structure coming into contact with the blocking mechanism 10. Shortly before contact, but at the latest, at the instant contact is made, the retaining elements 8 flex radially outwards into the recess 11 due to the force exerted by the spring 15 via the retaining shoulder 18 so that the retaining engagement is released. The flexing movement of the retaining elements 8 is assisted by their natural elastic rebound forces. The retaining shoulder 18 and/or the complementary shoulders 8a point at an angle to the longitudinal axis L so that they are able to slide on one another as soon as the retaining elements 8 are able to flex into the recess 11. Jamming is at least prevented by an inclined contour of the retaining shoulder 18 and/or the complementary shoulders 8a.

FIG. 3 illustrates the injector in the state immediately after the retaining engagement has been released and before the onset of the forward-driving movement of the plunger rod 16. The plunger rod 16 switches due to the pressure of spring 15 immediately from this transition state to the forward-driving movement. The support structure is retained in its proximal position relative to the casing structure 1 due to the contact pressure of the injector on the skin. As it moves in the forward-drive direction, the plunger rod 16 presses against the plunger 3 with its ram 17. Due to the static friction between the plunger 3 and the container 2, the container 2 moves in the support structure in the forward-drive direction V. The injection cannula 4 moves in conjunction with the container 2, piercing the cannula cover 20 during the course of this piercing movement, so that it is then inserted in the skin and, in some preferred embodiments, the tissue underneath the skin. During the course of the piercing movement, the container 2 is pushed past the blocking element 6 and is bent outwards as a result. The cannula cover 20 is also compressed. The cannula cover 20 restricts the piercing movement and hence the penetration depth of the injection cannula 4.

FIG. 4 illustrates the injector after the piercing movement but before the product has been dispensed. The piercing movement of the plunger rod 16 switches to the dispensing movement during which the product is dispensed at the latest after the injection cannula 4 has completed the piercing movement. In some preferred embodiments, the piercing movement of the injection cannula 4 is terminated before the plunger 3 starts the dispensing movement. The plunge rod 16 causes both movements due to its own forward-drive movement. In this respect, the spring 15 constitutes a piercing and dispensing spring.

FIG. 5 illustrates the injector after the container 2 has been completely emptied, i.e., after the dispensing process has been terminated but before the injection cannula 4 has been pulled out of the tissue. When the injection cannula 4 is now pulled out of the tissue, the needle guard 21 moves in the forward-drive direction V relative to the casing structure 1 due to the force of the spring 22. During the course of this movement, the needle guard 21 is moved in the forward-drive direction V back in front of the blocking element 6 by means of a stop shoulder. The blocking element 6 and the relevant stop shoulder of the needle guard 21 then lie axially opposite one another so that the blocking element 6 prevents the needle guard 21 from being retracted again and blocks the needle guard 21 in its protective position.

FIG. 6 illustrates the injector after use with the blocked needle guard 21. The injector may be designed as a disposable device and is disposed of once it has been used.

Figure 7:
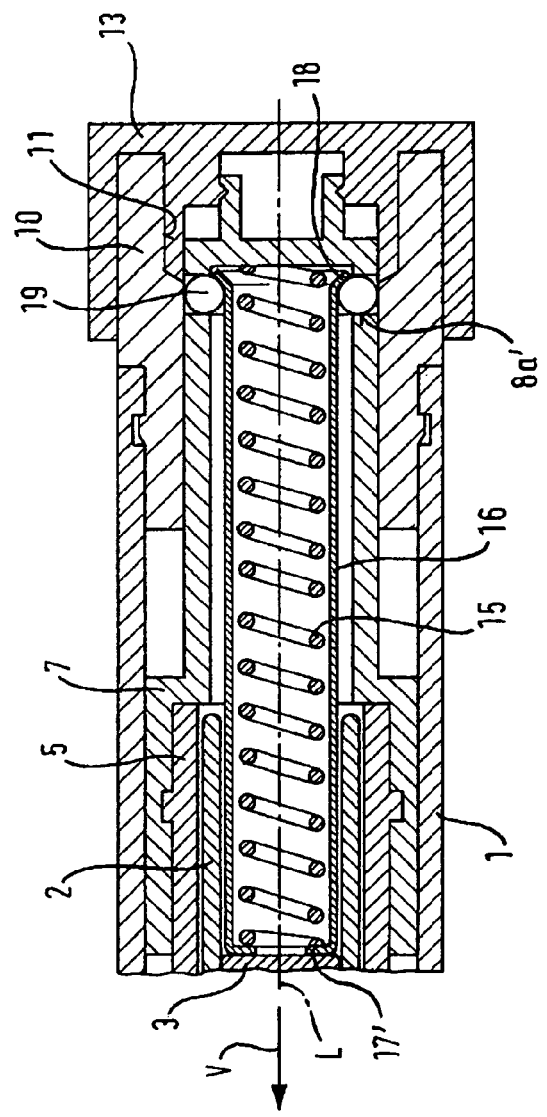
FIG. 7 illustrates a proximal or rear part of a modified automatic injector in accordance with the present invention.

FIG. 7 illustrates the proximal portion of a modified automatic injector, which differs from the injection device illustrated in FIGS. 1 to 6 due to the ram of the plunger rod 16 and the retaining engagement between the plunger rod 16 and the support structure. The ram 17' of the modified embodiment, illustrated as an example, is not formed by the sleeve shaft of the plunger rod 16 as a continuous base, but as a peripheral annular shoulder. The plunger rod 16 of the modified embodiment is again a metal sleeve. However, it is made by re-shaping a tubular piece. The sleeve shaft is the tubular piece in its not warped form. The ram 17' and the retaining shoulder 18 are respectively formed by a bending process, the ram 17' by pressing on a hollow die and the retaining shoulder by pressing against a widening die.

In the exemplary modified embodiment, the retaining engagement is not obtained between the retaining shoulder 18 and the support structure but by means of one, or in the embodiment illustrated, by several transmitting elements 19. The transmitting elements 19 might be ball bearings or cylindrical pins, for example, which are pressed in the forward-drive direction V by the spring 15 via the retaining shoulder 18 against a complementary shoulder of the support structure. The retaining engagement is released in the same way as that of the device illustrated in FIGS. 1 to 6, the only difference being that it is the transmitting elements 19 which flex into the recess 11 of the blocking mechanism 10 rather than a retaining element 8 formed by the support structure.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All equitably entitled.

The invention claimed is:

1. A device for administering an injectable product, comprising:
   a) a housing,
   b) a displaceably mounted product container accommodated by the housing, the product container containing the injectable product retained between an outlet and a plunger mounted therein so that the plunger can be displaced in a forward-drive direction in order to dispense the product,
   c) a plunger rod comprising a first end that acts on the plunger in the forward-drive direction and a second end opposite the first end, the second end comprising a widening that retains the plunger rod in a retained position in a retaining engagement, and
   d) a spring acting on the plunger rod in the forward-drive direction, wherein the plunger rod is held releasably in the retained position in the retaining engagement against the force of the spring, and wherein the spring projects into the container substantially as far as the plunger in the retained position.

2. A device as claimed in claim 1, wherein the plunger rod has a ram, the ram pushing against the plunger in the forward-drive direction to dispense the product.

3. A device as claimed in claim 2, wherein the ram forms a foremost end face of the plunger rod in the forward-drive direction.

4. A device as claimed in claim 1, wherein the plunger rod surrounds the spring.

5. A device as claimed in claim 4, wherein the plunger rod is a sleeve and the spring is supported on a shoulder which projects inwardly on a front end of the sleeve in the forward-drive direction and forms the foremost end face of the plunger rod.

6. A device as claimed in claim 4, wherein the plunger rod widening comprises a retaining shoulder extending at an angle with respect to the forward-drive direction with a directional component parallel with and a directional component perpendicular to the forward-drive direction.

7. A device as claimed in claim 4, wherein the plunger rod is a sleeve structure made from a semi-finished product by a plastic forming process.

8. A device as claimed in claim 4, wherein the plunger rod is formed as a single piece.

9. A device as claimed in claim 4, wherein a metallic material is used to make the plunger rod.

10. A device as claimed in claim 4, wherein the plunger rod is a deep-drawn part.

11. A device as claimed in claim 4, wherein the plunger rod is produced from a tubular piece by forming at least one end of the tubular piece.

12. A device as claimed in claim 1, further comprising a support structure which supports the product container so that the container is displaceable in the forward-drive direction.

13. A device as claimed in claim 12, wherein the support structure forms a support for the spring.

14. A device as claimed in claim 12, wherein the housing supports the support structure so that the support structure is displaceable in the direction opposite the forward-drive direction.

15. A device as claimed in claim 12, wherein the plunger rod is in the retaining engagement with the support structure.

16. A device as claimed in claim 1, wherein the plunger rod widening comprises a retaining shoulder and the device comprises a complementary shoulder fixed so that it can not be displaced in the forward-drive direction, at least when the plunger rod is in the retained position.

17. A device as claimed in claim 16, wherein the retaining shoulder and the complementary shoulder are in direct contact with one another in the retaining engagement.

18. The device according to claim 16, wherein a transmitting device causes the retaining engagement between the retaining shoulder and the complementary shoulder.

19. A device as claimed in claim 18, wherein a blocking mechanism is provided, which blocks one of the retaining shoulder and complementary shoulder in the retaining engagement.

20. A device for administering an injectable product, comprising a housing, a displaceably mounted product container associated with the housing, a plunger in the container for retaining the injectable product in the product container and so that the plunger can be displaced in a forward-drive direction to administer the product, a plunger rod having a first end acting on the plunger in the forward-drive direction and a second end opposite the first end having a widening by which the plunger rod is held in a releasable retained position, and a spring acting on the plunger rod in the forward-drive direction, the plunger rod releasably held in the retained position in a retaining engagement against the force of the spring, wherein the spring projects into the container substantially as far as the plunger in the retained position.

21. A device for administering an injectable product, comprising:
a) a housing,
b) a displaceably mounted product container accommodated by the housing, the product container containing the injectable product retained between an outlet and a plunger mounted therein so that the plunger can be displaced in a forward-drive direction in order to dispense the product,
c) a plunger rod having a first end acting on the plunger in the forward-drive direction and a second end opposite the first end having an axial, open funnel shape widening in a direction opposite to the forward-drive direction,
d) a spring acting on the plunger rod in the forward-drive direction, wherein the plunger rod is held releasably by the axial, open funnel shape in a retained position in a retaining engagement against the force of the spring, and wherein the spring projects into the container substantially as far as the plunger in the retained position, and
e) a cannula cover disposed on a distal end of the container over an injection cannula.

22. A device as claimed in claim 21, wherein the cannula cover comprises an axially flexible rubber sleeve.

23. A device as claimed in claim 22, wherein the cannula cover restricts penetration depth of the injection cannula during dispensement of the product.

* * * * *